(12) United States Patent
Takacs

(10) Patent No.: US 7,847,114 B2
(45) Date of Patent: Dec. 7, 2010

(54) SELF-ASSEMBLED HETEROLEPTIC CHIRAL LIGANDS, ASYMMETRIC CATALYST SYSTEMS AND METHODS

(75) Inventor: James M. Takacs, Lincoln, NE (US)

(73) Assignee: University of Nebraska at Lincoln, Lincoln, NE (US)

( * ) Notice: Subject to any disclaimer, the term of this patent is extended or adjusted under 35 U.S.C. 154(b) by 1017 days.

(21) Appl. No.: 11/316,358

(22) Filed: Dec. 23, 2005

(65) Prior Publication Data
US 2006/0167294 A1    Jul. 27, 2006

Related U.S. Application Data

(60) Provisional application No. 60/638,760, filed on Dec. 23, 2004.

(51) Int. Cl.
C07F 7/24 (2006.01)
(52) U.S. Cl. .......................................... 556/1; 502/167
(58) Field of Classification Search ...................... 556/1; 502/102
See application file for complete search history.

(56) References Cited

PUBLICATIONS

Bardaji et al., Synthesis, Structural Characterization, and Luminescence Studies of Gold(I) and Gold(III) Complexes with a Triphosphine Ligand, Inorganic Chemistry (1998), 37(20), 5125-5130.*
Jurkschat et al., Synthesis, structure, and reactivity of novel intramolecularly coordinated organolead(II) compounds, European Journal of Inorganic Chemistry (2003), (19), 3563-3571.*
Holliday, B. J.; Mirkin, C. A "Strategies for the construction of supramolecular compounds through coordination chemistry," *Angew. Chem. Int. Ed.* 2001, 40, 2022-2043.
Leininger, S.; Olenyuk, B.; Stang, P. J. "Self-Assembly of Discrete Cyclic Nanostructures Mediated by Transition Metals," *Chem. Rev.* 2000, 100, 853-90.
Yoshizawa, M.; Takeyama, Y.; Kusukawa, T.; Fujita, M. "Cavity-directed, highly stereoselective [2+2] photodimerization of olefins within self-assembled coordination cages," *Angew. Chem. Int. Ed.* 2002, 41, 1347-1349.
Larsen, J.; Rasmussen, B. S.; Hazell, R. G.; Skrydstrup, T. "Preparation of a novel diphosphinepalladium macrocyclic complex possessing a molecular recognition site. Oxidative addition studies," *Chem. Commun. (Cambridge)* 2004, 202-203.
Braunstein, P.; Clerc, G.; Morise, X. "Cyclopropanation and Diels-Alder reactions catalyzed by the first heterobimetallic complexes with bridging phosphinooxazoline ligands," *New J. Chem.* 2003, 27, 68-72.
Braunstein, P.; Clerc, G.; Morise, X.; Welter, R.; Mantovani, G. "Phosphinooxazolines as assembling ligands in heterometallic complexes," *Dalton Transactions* 2003, 1601-1605.
Breit, B.; Seiche, W. "Hydrogen Bonding as a Construction Element for Bidentate Donor Ligands in Homogeneous Catalysis: Regioselective Hydroformylation of Terminal Alkenes," *J. Am. Chem. Soc.* 2003, 125, 6608-6609.

Siagt, V. F.; Van Leeuwen, P. W. N. M.; Reek, J. N. H. "Bidentate Ligands Formed by Self Assembly," *Chem. Commun. (Cambridge)* 2003, 2474-2475.
Hua, J.; Un, W. "Chiral Metallacyclophanes: Self-Assembly, Characterization, and Application in Asymmetric Catalysis," *Org. Lett.* 2004, 6, 861-864.
Jiang, H.; Hu, A; Un, W. "A chiral metallacyclophane for asymmetric catalysis," *Chem. Commun. (Cambridge)* 2003, 96-97.
Lee, S. J.; Hu, A.; Un, W. "The First Chiral Organometallic Triangle for Asymmetric Catalysis," *J. Am. Chem. Soc.* 2002, 124, 12948-12949.
Giannneschi, N. C.; Bertin, P. A.; Nguyen, S. T.; Mirkin, C. A; Zakharov, L. N.; Rheingold, A L. "A Supramolecular Approach to an Allosteric Catalyst," *J. Am. Chem. Soc.* 2003, 125, 10508-10509.
Mikami, K.; Tereda, M.; Korenaga, T.; Matsumoto, Y.; Ueki, M.; Angeluad, R. "Asymmetric activation," *Angew. Chem. Int. Ed.* 2000, 39, 3532-3556.
Mikami, K.; Matsukawa, S.; Volk, T.; Terada, M. "Self-assembly of several components into a highly enantioselective Ti catalyst for carbonyl-ene reactions," *Angew. Chem., Int. Ed. Engl.* 1998, 36, 2768-2771.
Shin A. Moteki and James M. Takacs, "Exploiting Self-Assembly for Ligand-Scaffold Optimization: Substrate-Tailored Ligands for Efficient Catalytic Asymmetric Hydroboration", Angew. Chem. Int. Ed. 2008, 47, pp. 894-897.
James M. Takacs, Kittichai Chaiseeda, Shin A. Moteki, D. Sahadeva Reddy, Di Wu & Kusumlata Chandra; "Rhodium-catalyzed Asymmetric Hydrogenation Using Self-Assembled Chiral Bidentate Ligands"; pp. 1-9, Dep't of Chemistry, Univ. of Nebraska-Lincoln, Lincoln, NE 98588, 2006.
James M. Takacs, D. Sahadeva Reddy, Shin A. Moteki, Di Wu & Hector Palencia; "Asymmetric Catalysis Using Self-Assembled Chiral Bidentate P,P-Ligands"; Department of Chemistry, Univ. of Nebraska-Lincoln, Nebraska, JACS Communications, received Jan. 8, 2004; J.Am.Chem.Soc. 2004, 126; 4494-4495.

* cited by examiner

*Primary Examiner*—Daniel M Sullivan
*Assistant Examiner*—Chukwuma O Nwaonicha
(74) *Attorney, Agent, or Firm*—Gianna J. Arnold; Miles & Stockbridge P.C.

(57) ABSTRACT

A method of synthesizing a heteroleptic, multiple metal-containing metallocyclic catalyst, particularly suited for asymmetric catalysis, comprising combining a plurality of plural functional group-containing, monodentate ligands of complementary chirality, said plural functional groups being tethered to each other by tethers in the presence of a scaffold-structural metal Ms or derivative thereof, wherein at least one functional group on each ligand combines to ligate $M_s$ to form a bidentate, $M_s$ centered ligand scaffold containing the remaining functional groups and combining said bidentate ligand scaffold with a catalytic metal $M_c$ or derivative thereof whereby the remaining functional groups combine to ligate $M_c$, thereby forming said catalyst.

18 Claims, 12 Drawing Sheets

SELF-ASSEMBLED HETEROLEPTIC CHIRAL LIGANDS, ASYMMETRIC CATALYST SYSTEMS AND METHODS

CROSS-REFERENCE TO RELATED APPLICATIONS

This application claims the benefit of priority of Provisional Application Ser. No. 60/638,760 filed Dec. 23, 2004.

This invention was made with Government support under N00014-05-1-0527 awarded by the Navy/ONR and under GM070939 awarded by the National Institute of Health. The Government has certain rights in the invention.

FIELD OF THE INVENTION

The invention relates to novel catalysts and catalysis reactions employing same.

BACKGROUND OF THE INVENTION

Catalysis and asymmetric catalysis are processes of commercial importance in synthetic chemistry. The development of efficient methods to enable the reliable, stereocontrolled synthesis of small molecule target structures is an important goal relevant to the synthesis of compounds of commercial interest such as pharmaceutical drugs, agrochemicals and compounds with interesting materials properties. Asymmetric catalysis plays an important role in meeting this goal, and while tremendous advances have been realized in this rapidly moving field of research, significant problems remain. Among the most important of these problems are the need for (i) better substrate generality and/or more precisely substrate tunable catalyst systems, (ii) better catalyst stability (i.e., higher turnover number, TON), and (iii) better catalyst efficiency (i.e., higher turnover frequency, TOF). Solutions to these problems hinge on discovering and optimizing new ligands and catalyst systems, and understanding the reasons for their effectiveness. Most modular approaches start with one or a small set of scaffolds (equivalently, backbones or templates) and sequentially append the plural ligating substituents. The idea is to systematically vary the nature of the ligating groups (i.e., vary their elemental identity, shape, steric demand, and electronic character) to tune or optimize the asymmetric environment at the site of catalysis as well as define the nature of the metal-ligand interaction.

An interesting scaffold is selected and one sequentially couples a series of ligating substituents in ligand diversification steps. The ligands are then evaluated in the reaction(s) of interest. This linear synthetic approach employed with this strategy has worked well; however, the necessity for preparing as few as 20-25 chiral ligands using this approach greatly reduces the efficiency thereof. Limitations such as these demand new approaches to the problem.

For example, metal-directed self-assembly has been a very active area of research over the past decade and as a result facile routes to a wide variety of multiple metal containing metallocycles and metallocages have been defined [Holliday, B. J.; Mirkin, C. A "Strategies for the construction of supramolecular compounds through coordination chemistry," *Angew. Chem. Int. Ed.* 2001, 40, 2022-2043; Leininger, S.; Olenyuk, B.; Stang, P. J. "Self-Assembly of Discrete Cyclic Nanostructures Mediated by Transition Metals," *Chem. Rev.* 2000, 100,853-907]. The potential for novel uses of such structures has long been the goal of the research in this area, but to date, the preparation of functional structures is still rather rare [Yoshizawa, M.; Takeyama, Y.; Kusukawa, T.; Fujita, M. "Cavity-directed, highly stereoselective [2+2] photodimerization of olefins within self-assembled coordination cages," *Angew. Chem. Int. Ed.* 2002,41,1347-1349]. Recently, several reports have appeared wherein self-assembly is used to generate novel bidentate ligands [Larsen, J.; Rasmussen, B. S.; Hazell, R. G.; Skrydstrup, T. "Preparation of a novel diphosphine-palladium macrocyclic complex possessing a molecular recognition site. Oxidative addition studies," *Chem. Commun. (Cambridge)* 2004, 202-203; Braunstein, P.; Clerc, G.; Morise, X. "Cyclopropanation and Diels-Alder reactions catalyzed by the first heterobimetallic complexes with bridging phosphinooxazoline ligands," *New J. Chem.* 2003, 27, 68-72; Braunstein, P.; Clerc, G.; Morise, X.; Welter, R.; Mantovani, G. "Phosphinooxazolines as assembling ligands in heterometallic complexes," *Dalton Transactions* 2003, 1601-1605; Breit, B.; Seiche, W. "Hydrogen Bonding as a Construction Element for Bidentate Donor Ligands in Homogeneous Catalysis: Regioselective Hydroformylation of Terminal Alkenes," *J. Am. Chem. Soc.* 2003, 125, 6608-6609; Siagt, V. F.; Van Leeuwen, P. W. N. M.; Reek, J. N. H. "Bidentate Ligands Formed by Self Assembly," *Chem. Commun. (Cambridge)* 2003,2474-2475; Hua, J.; Un, W. "Chiral Metallacyclophanes: Self-Assembly, Characterization, and Application in Asymmetric Catalysis," *Org. Lett.* 2004, 6, 861-864; Jiang, H.; Hu, A; Un, W. "A chiral metallacyclophane for asymmetric catalysis," *Chem. Commun. (Cambridge)* 2003, 96-97; Lee, S. J.; Hu, A.; Un, W. "The First Chiral Organometallic Triangle for Asymmetric Catalysis," *J. Am. Chem. Soc.* 2002, 124,12948-12949] and catalyst systems [Gianneschi, N. C.; Bertin, P. A.; Nguyen, S. T.; Mirkin, C. A; Zakharov, L. N.; Rheingold, A L. "A Supramolecular Approach to an Allosteric Catalyst," *J. Am. Chem. Soc.* 2003, 125, 10508-10509; Mikami, K.; Tereda, M.; Korenaga, T.; Matsumoto, Y.; Ueki, M.; Angeluad, R. "Asymmetric activation," *Angew. Chem. Int. Ed.* 2000, 39, 3532-3556; Mikami, K.; Matsukawa, S.; Volk, T.; Terada, M. "Self-assembly of several components into a highly enantioselective Ti catalyst for carbonyl-ene reactions," *Angew. Chem., Int. Ed. Engl.* 1998, 36, 2768-2771]. The general approach employed is outlined in FIG. 1. A metal-containing (or multiple metal-containing) scaffold is synthesized and combined with two or more bifunctional subunits leading to formation of the self-assembled ligand (SAL) 1. In general, the ligands prepared via this approach are symmetric since the ligating groups incorporated are identical; i.e., homoleptic complexes (i.e., two identical ligating groups) are formed. Several research-groups recently described successful efforts to prepare chiral SALs for asymmetric catalysis via the above described metal-directed self-assembly.

It is an object of the invention to provide novel asymmetric catalysts prepared by a novel combinatorial method.

It is a further object to provide novel catalyst systems containing the novel asymmetric catalysts.

It is a still further object of the invention to provide novel catalysis methods employing the novel asymmetric catalysts and catalyst systems of the invention.

SUMMARY OF THE INVENTION

The above and other objects are realized by the present invention, one embodiment of which relates to a method of synthesizing a heteroleptic, multiple metal-containing metallocyclic catalyst, particularly suited for asymmetric catalysis, comprising combining a plurality of plural functional group-containing, monodentate ligands of complementary chirality, the plural functional groups being tethered to each other by tethers in the presence of a scaffold-structural metal Ms or derivative thereof, wherein at least one functional group on each ligand combines to ligate $M_s$ to form a bidentate, $M_s$ centered ligand scaffold containing the remaining functional groups and combining the bidentate ligand scaffold with a catalytic metal $M_c$ or derivative thereof whereby the remaining functional groups combine to ligate $M_c$, thereby forming said catalyst.

A further embodiment of the invention concerns a method of synthesizing a heteroleptic, multiple metal-containing metallocyclic catalyst, particularly suited for asymmetric catalysis, comprising combining, in the presence of a scaffold-structural metal Ms or a derivative thereof, plural bifunctional group-containing, monodentate ligands of complementary chirality having the formulae:

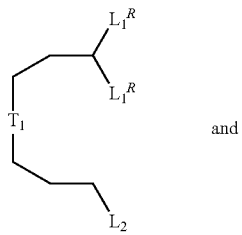

[1]

and

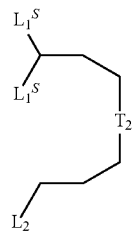

[2]

wherein: the $L_1$s are ligating functional groups of complementary chiralty capable of ligating a scaffold-structural metal $M_s$, the $L_2$s are ligating functional groups capable of ligating a catalytic metal $M_c$ $_{and\ T1}$ and $T_2$ are tethers linking said $L_1$s to said $L_2$s, to form a bidentate, $M_s$-centered ligand scaffold having the formula:

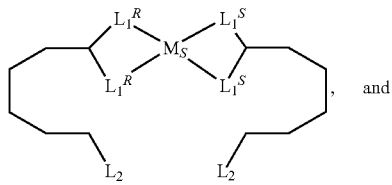

, and combining the bidentate ligand scaffold with a catalytic metal $M_c$ or derivative thereof whereby the remaining functional groups, $L_2$ combine to ligate $M_c$, thereby forming the catalyst having the formula:

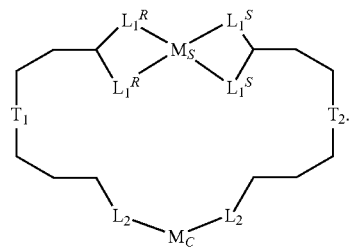

Additional embodiments of the invention comprise the asymmetric catalysts formed by the above-described methods.

Still further embodiments of the invention concern catalyst systems comprising the above asymmetric catalysts supported on suitable substrates for use in catalysis methods.

More embodiments of the invention relate to chemical catalysis methods employing the above described asymmetric catalysts and catalyst systems.

DETAILED DESCRIPTION OF THE INVENTION

The present invention is predicated on the discovery of a method of using metal-directed multi-component self-assembly in a new combinatorial approach to the design and optimization of ligands and catalyst systems. The modular bidentate ligand design of the invention is based on the scientific hypothesis that the nature of the ligating group can be used to define a chiral surface and the electronic nature of the metal-ligand interaction, and that, then, the ligand scaffold can be varied through combinatorial synthesis to define the optimal orientation of that chiral surface (ligating group) for efficient asymmetric catalysis.

Ultimately, the goal of all chiral ligand designs is to (i) create an appropriate "chiral pocket" around the metal to direct stereochemistry, and (ii) impart the appropriate electronic characteristics at the metal center for efficient catalysis. The present invention achieves these goals utilizing a convergent approach to ligand scaffold optimization using metal-directed multi-component self-assembly. Multi-component reactions have garnered much attention as synthetic strategies due to their potential to increase diversity while simplifying the synthesis of structurally complex compounds. Multi-component self-assembly offers the same potential benefits in ligand synthesis of the present invention.

Figure 1:
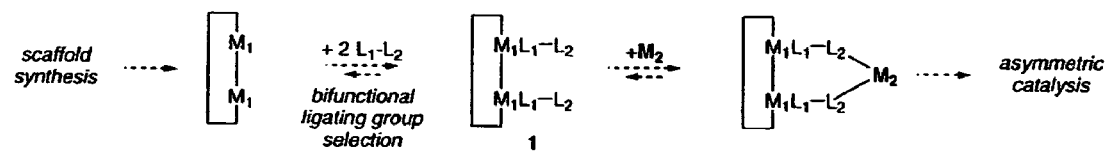
FIGS. 1-4, 6-12 set forth reaction schemes for various of the methods described herein.
Figure 2:
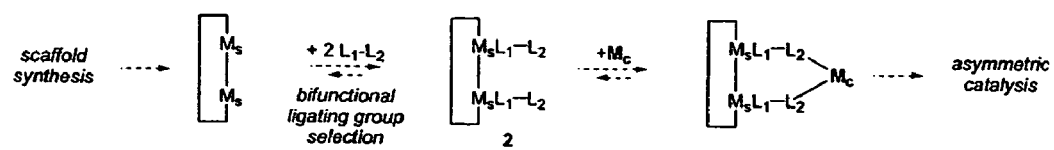

The method of the invention comprises three basic steps (FIG. 2). One of the novel aspects of the invention resides in the fact that the ligand scaffold is established in the last step of the synthesis. The first two steps parallel that of the typical modular approach, except that they are applied to separate halves of the ultimate bidentate ligand; (i) selecting the series of tether subunits begins to define the scaffold and (ii) selecting the series of ligating groups begins to define both the nature of the metal ligand interaction and the topology around the catalytic metal. The third step, the convergent self-assembly, connects 'bifunctional ligands' to fully establish both the scaffold as well as the precise combination of ligating groups in self-assembled ligand (SAL) 9. The inventive method is based upon forming a heteroleptic metal complex and can be carried out in a combinatorial fashion. Self-assembly leaves a second set of ligating groups now suitably disposed to bind a second metal. Addition of that catalytic metal (Me) completes the bimetallic catalyst 10. Other modular ligand designs attach ligating groups as substituents to a preformed scaffold. Here, metal-directed self-assembly generates the scaffold as the final step, and as such, allows the rapid assembly of a diverse set of scaffolds and more thoroughly optimize its structure.

Figure 3:
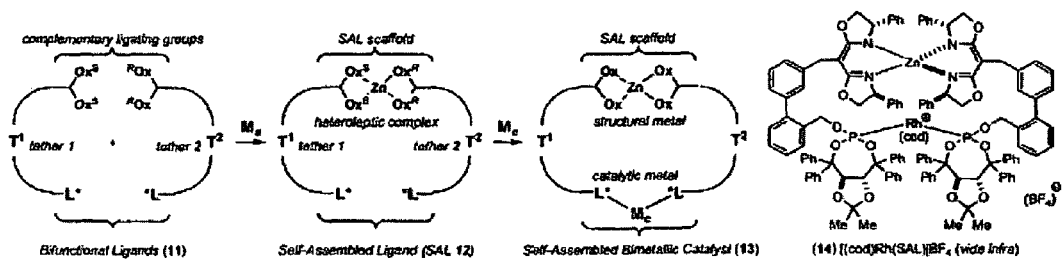

The heteroleptic self-assembly approach of the invention is fundamentally different from the modular approach of the prior art and provides a powerful approach to the construction of novel ligand libraries. The design concept of the invention is illustrated in more detail in FIG. 3. To execute the approach, a simple, efficient, and mild method was designed for the metal-directed heteroleptic self-assembly via the selective zinc(II)-complexation of bisoxazoline (box) subunits of complementary chirality. The box-tethered chiral monodentate ligands 11 were used as the bifunctional ligands. Two independent bifunctional ligands bearing box subunits of opposite chirality self-assemble upon treatment with $Zn(OAc)_2$ to give a neutral complex, a chiral bidentate SAL 12. Each independent half in this convergent route is in turn prepared from three modules, (i) an (R) or (S)-box subunit; (ii) a tether subunit; and (iii) a ligating group. As exemplified below, the latter is introduced in the penultimate or a late stage step of the synthesis, with combinatorial zinc-directed self-assembly as the final step. Thus, there exists the capacity for extensive diversification in the last two steps of the synthesis with self-assembly establishing both the final structure of the ligand scaffold and the exact combination of ligating groups in a SAL library. Structure 14 (discussed in detail below) illustrates how the concept of the invention is reduced to practice.

It is known that metalloenzymes often use two types of metals to carry out their function.

Structural metals help generate the three-dimensional structure, and a second metal binding site is often part of that structure. An independent, catalytic metal binds to this latter site to carry out the required chemistry. The system of the invention mimics that strategy. A neutral, heteroleptic $(box)_2$ Zn complex, wherein the zinc serves as a structural metal. At the same time, the process of self-assembly constructs a chiral binding site for a second, independent metal to bind and effect catalysis.

Any suitable metal or combination of metals may be employed in the practice of the invention, including, for example, Zn, Co, Rh, Mg, Ca, Ba, Ti, Zr, and the like.

Also, any suitable ligating group may be employed in the practice of the invention, including but not limited to those exemplified herein. Suitable tethering groups also include, but are not limited to, those exemplified below. Preferred tethers are alkyl (e.g., substituted alkane and cycloalkane) and aryl (e.g., substituted phenyl and biphenyl) groups.

The self-assembled chiral catalysts and catalyst systems of the invention may be employed in any chemical process catalyzed by any ligated metal catalyst, including, but not limited to, those exemplified herein as well as rhodium- and iridium-catalyzed asymmetric hydrogenation of alkenes; rhodium-, iridium-, and ruthenium-catalyzed transfer hydrogenation of alkenes, carbonyls and imines; rhodium-, iridium-, and ruthenium-catalyzed dehydrogenation of alcohols; rhodium- and iridium-catalyzed asymmetric hydroboration of alkenes; palladium-catalyzed asymmetric allylic alkylation and aminations; palladium-, rhodium-, and iridium-catalyzed asymmetric enyne cycloisomerizations; palladium-, rhodium-, and iridium-catalyzed asymmetric cyclizations and cycloisomerizations; rhodium-catalyzed alkene hydroformylation; and the like.

The need to carry out efficient enantioselective catalysis is frequently encountered, for example, in chemical discovery and process research (such as commonly encountered in the synthesis of pharmaceuticals and pharmaceutical intermediates), and for each particular substrate, the typical approach is to screen a series of chiral ligands looking for the most suitable catalyst system. The present invention, embodying the use of SALs introduces a new paradigm for chiral catalyst development, develops a niche for custom asymmetric catalysts, for example, for asymmetric allylic amination, asymmetric hydrogenation, and asymmetric hydroboration. Moreover, the chiral ligand libraries (exemplified below) produced also find applications in numerous other metal-catalyzed reactions, provided, of course, that the reactions do not require the use of reagents that have deleterious effects on the catalysts.

Those skilled in the art will realize that the SAL concept described herein may be extended from one that focuses exclusively on the design of chiral bidentate ligands to include polydentate ligands, for example, tri- or tetradentate ligands. One box derivative will contribute a bidentate ligand upon self-assembly, the other a mono- or bidentate ligand as needed, for example, the development of polydentate chiral SALs, particularly for expanding the chiral ligand systems for lanthanide catalysis. The invention is also applicable for developing bifunctional catalysts systems, reversible reagent delivery, and sequenced multi-component reactions; indeed, virtually any combinatorial chemical synthesis.

EXAMPLE 1

Figure 4:
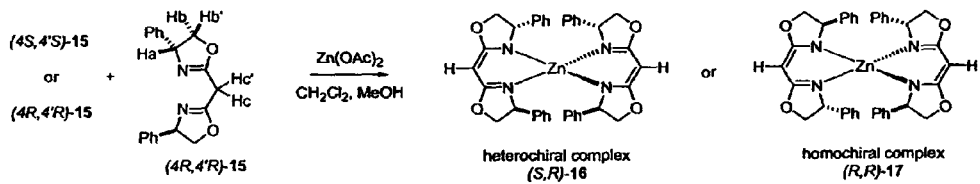

Referring to FIG. 4, the neutral, homochiral complex (R,R-17) is formed by stirring two equivalents of (4R,4'R)-15 with $Zn(OAc)_2$. $Zn(OAc)_2$ serves a dual role in the reaction, simultaneously delivering the metal center and the required base. However, when a racemic mixture of box ligands (i.e., one equivalent each of (4S,4'S)-15 and (4R,4'R)-15) is combined with $Zn(OAc)_2$, three complexes could theoretically form, the homochiral complexes (S,S)— and (R,R)-17 (i.e., chiral self-recognition) and the heterochiral complex (S,R)-16 (i.e., chiral self-discrimination). The tetrahedral coordination geometry of zinc(II) strongly favors self-discrimination in this case. Indeed, only the neutral, heterochiral complex (S,R)-16 is observed.

EXAMPLE 2

Figure 5:
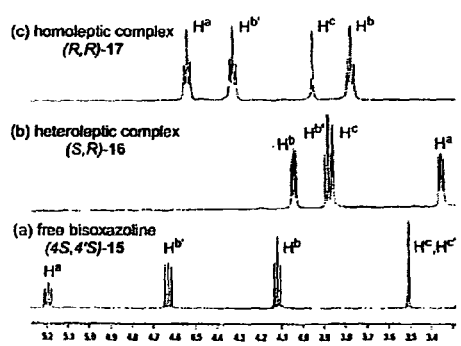
FIGS. 5 and 16 set forth analytical data for various of the compounds described herein.
Figure 5:
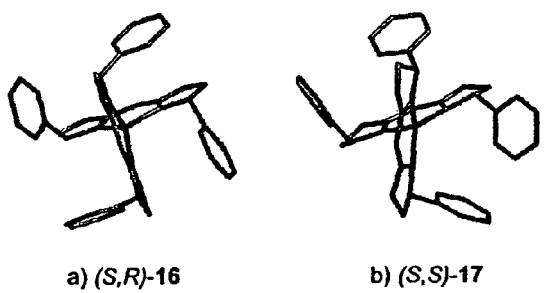

FIG. 5 compares the 1H NMR spectrum for the free box ligand 15 (trace a) to those of the heterochiral ((S,R)-16, trace b) and homochiral complexes ((R,R)-17, trace c). These spectra show that the homochiral and heterochiral complexes are distinctly different in solution, and to the level of NMR detection, the combination of (4S,4'S)-15 and (4R,4'R)-15 with $Zn(OAc)_2$ affords exclusively the heterochiral complex. Of particular note in the spectrum of (S,R)-16 is the dramatic upfield shift for the hydrogen on the phenyl-bearing carbon of the dihydrooxazole ring ($H^a$; see structure 15, FIG. 4). It is highly shielded in the heterochiral complex relative to the free ligand or homochiral complex.

EXAMPLE 3

Figure 6:
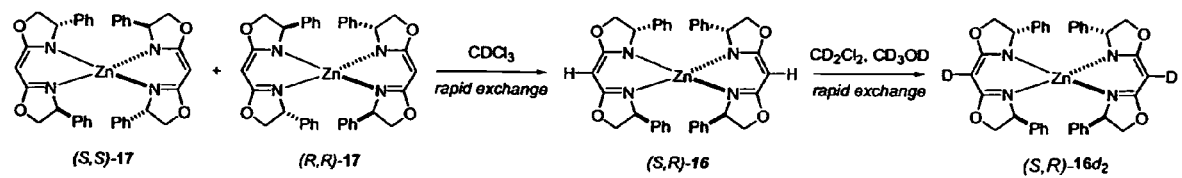

To better understand the factors favoring self-discrimination over self-recognition, crystals of (S,R)-16 and (S,S)-17 were grown and their structures determined by x-ray analysis (FIG. 6). The heterochiral complex (S,R)-16 exhibits near perfect tetrahedral coordination while the homochiral complex (S,S)-17, for which there are two closely related conformers in the unit cell, distorts from tetrahedral coordination to minimize steric interactions between the phenyl substituents of the two box ligands. Otherwise, the bond lengths and angles vary little between the two complexes. The crystal structures are consistent with the NMR data, particularly the positioning of the phenyl groups in the heterochiral complex (S,R)-16 so as to shield the hydrogen on the phenyl-bearing carbon of the dihydrooxazole ring ($H^a$).

EXAMPLE 4

Figure 7:
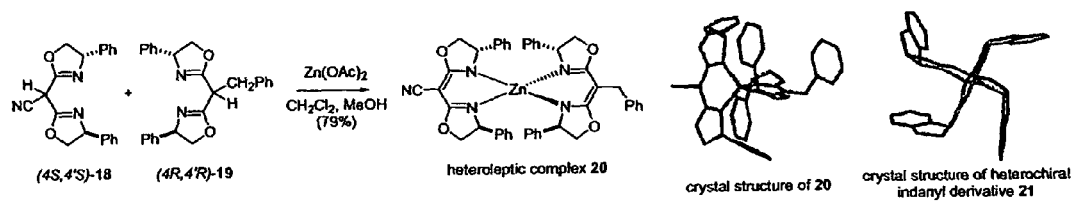

Heterochiral complexes such as (S,R)-16 are meso by inversion symmetry and hence achiral. Nevertheless, the process of chiral self-discrimination is inherently one of heteroleptic self-assembly (i.e., non-identical groups bond to the metal) and is not restricted to combining pairs of enantiomers. Pseudo-enantiomers can combine similarly to afford products lacking a center of inversion. To illustrate this and the potential versatility for preparing chiral, heteroleptic complexes, the pseudo-racemic combination (4S,4'S)-18 and (4R,4'R)-19 was used to prepare the mixed cyano/benzyl-substituted complex 20 (FIG. 7). In spite of the complementary chirality of the box moieties, complex 20 lacks inversion symmetry and is chiral, exhibiting a large optical rotation, $[\alpha]_D = -203°$ (c=0.75, $CH_2Cl_2$).

EXAMPLE 5

The neutral zinc complexes prove to be quite remarkable compounds. Complexation is reversible in the presence of a proton source, for example, adding another (R)- or (S)-box derivative leads to rapid substitution, and mixing equal amounts of the enantiomeric homochiral complexes 17 leads to their rapid disproportionation (FIG. 6). Complete conversion to the heterochiral complex (R,S)-16 as judged by 1H NMR again indicates that the heterochiral complex is the thermodynamic sink. The neutral metal complexes are typically freely soluble in a variety of organic solvents (e.g., toluene, $CH_2Cl_2$, $CHCl_3$, THF, dioxane, and acetonitrile) and partially soluble in methanol. They are generally insoluble in hexanes, diethyl ether or cold methanol, and these latter organic solvents can be used to precipitate the complex from other solvents and/or wash the precipitated complex. It was surprising to find that, in some cases, the complexes can be subjected to column chromatography on silica (1% MeOH in $CHCl_3$ eluent) with little or no loss of zinc. Complex 16 is insoluble, but stable toward water, and can be subjected to extractive workup. Drying the organic phase with anhydrous $Na_2SO_4$ does not affect metal exchange. The complex is not completely inert toward protic solvents. For example, adding $CD_3OD$ to a solution of (S,R)-16 ($CD_2Cl_2$) shows complete H/D exchange by the time the 1H NMR spectrum is recorded.

EXAMPLE 6

The facile formation of a heterochiral complex is not limited to zinc. The corresponding heterochiral Co(II) complex was prepared. Its crystal structure is virtually superimposable on that of the zinc structure.

EXAMPLE 7

Self-assembly is also not limited to methylene box substrates or to the 4-phenyl-substituted box ligands illustrated. Corresponding complexes from 4,5-diphenyl and indanyl box derivatives have been prepared as well; for example, the crystal structure of the heterochiral (indanylbox)$_2$Zn complex 21 is shown above (FIG. 7).

EXAMPLE 8

It was found that the heterochiral (box)$_2$Zn complex, once formed, is stable toward exchange with several common ligands (e.g., 2,2'-isopropylidenebis(4-phenyl-2-oxazline), $Ph_3P$, BINAP, BINOL and diethyl tartrate). Furthermore, several potential ligands (i.e., 2,2'-isopropylidenebis(4-phenyl-2-oxazline), $Ph_3P$, CY3P, dppe) were tested in direct competition and do not to interfere with formation of the heterochiral complex. Their chemical characteristics, the structural studies, and their self-sorting and stability tests gave confidence that neutral, heterochiral (box)$_2$Zn complexes would remain intact and could be used in the presence of other suitable ligands. Their preparation is simple: mix the two enantiomeric box derivatives with Zn(OAch, remove the solvent ($CH_2Cl_2$/MeOH), triturate with methanol, and wash the resulting solid with methanol. The synthetic yields are high (typically 70-90%), and examination of the crude product reveals no side products. Mechanical losses probably account for the less than perfect isolated yields obtained.

EXAMPLE 9

Figure 8:
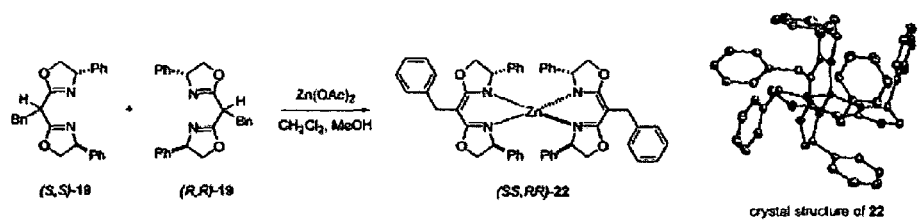

To get a better idea of the tether structure that would be needed to realize the approach in FIGS. 7 and 8 the heterochiral (benzylBox)$_2$Zn complex 22 (FIG. 8) was prepared and crystallized. By analysis of its crystal structure, and from manipulating that structure in Chem3D, it is apparent that the appended benzyl groups are of sufficient length to extend beyond the bulk of the (boxh)2Zn core, i.e., the benzyl groups can freely rotate and extend beyond the metal complex core. In fact, the core is quite compact; its end-to-end length is a little shorter than that of biphenyl. It was reasoned that substituted benzyl or biphenyl tethers should extend a tethered ligating group beyond the core and permit chelation as depicted schematically in FIGS. 7 and 8. The complex is also inherently a rather rigid structural element, contrary to what might be predicted. There is only one rotational degree of freedom relating the positions of the two benzyl substituents (i.e., would be tethers), two independent rotatable bonds but since they lie along the same axis it introduces a just single rotational degree of freedom.

EXAMPLE 10

Figure 9:
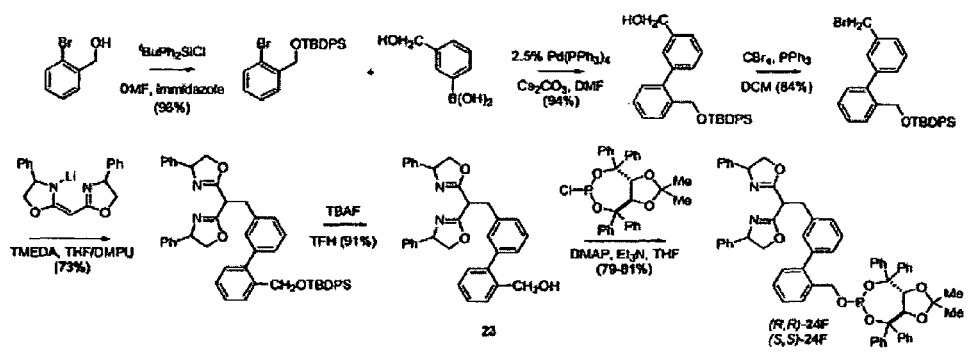

In light of the crystal structure of 22 and with an eye toward keeping the tether subunits relatively rigid, a series of substituted benzyl and biphenyl tethers was focused on for preparing SALs (FIG. 9). The synthetic route is illustrated for the preparation of 24F. The key step is mono-alkylation of the box subunit with a substituted benzyl bromide bearing a pendant silyl-protected hydroxyl substituent. For these initial studies, the derivative was prepared bearing a pendant TADDOL-derived monophosphite. Deprotection of the silyl ether followed by coupling with ((R,R)-TADDOL)PCI affords the desired bifunctional box-(TADDOL)phosphite conjugate 24F. The six step synthesis is quite efficient, and, typically 5-10 mmol of the penultimate intermediate, the alcohol 23, is prepared.

EXAMPLE 11

Figure 10:
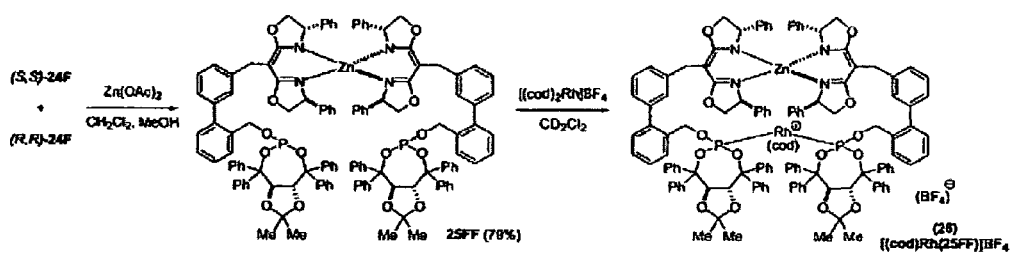

Treating the combination of (S,S)-24F and (R,R)-24F with $Zn(Oac)_2$ affords the pseudo-C2-symmetric complex 25FF (FIG. 10). The reaction is carried out by mixing the two diastereomeric bifunctional ligands (24F) with $Zn(Oac)_2$, removing the solvent ($CH_2Cl_2$/MeOH), triturating with methanol, and washing the resulting solid with methanol. The following data support its structural assignment. (1) The two diastereomeric bifunctional ligands (24F) are freely soluble in methanol, 25FF is not; the recovery of 25FF is high (79%). (2) The optical rotation of 25FF is lower than either of the 24F diastereomers. (3) 25FF melts with decomposition at a temperature 25-30 degrees higher than the melting points of the 24F diastereomers. (4) The HRMS matches for the parent ion of 25FF; the experimental and simulated isotope distribution patterns match. (5) The 1H and 13C NMR spectra are consistent with an overall pseudo-$C_2$-symmetric structure and show the expected elements in common 22, the dibenzyl box model compound for which the crystal structure is known. (6) The 31p NMR spectrum of 25FF shows a single resonance at 130.2 ppm, similar to that of its precursor (S,S)-24F (130.7 ppm).

EXAMPLE 12

Having formed 25FF, the crucial question is whether the pendant phosphites can coordinate a second metal. To test this, 25FF was treated with an equivalent of $[(cod)_2Rh]BF_4$. The $^{31}P$ NMR signal at 130.2 ppm, characteristic of a free phosphite, is lost and a new doublet appears at 112.7 ppm ($J_{Rh,P}$=248.6 Hz). The results are consistent with the formation of the chiral heterobimetallic rhodium complex [(cod)Rh(25FF)]$BF_4$ (26). Demonstrating that SAL 25FF forms a rhodium(l) complex is of particular relevance to, for example, (SAL)RhX-catalyzed asymmetric hydroboration reactions.

EXAMPLE 13

Figure 11:
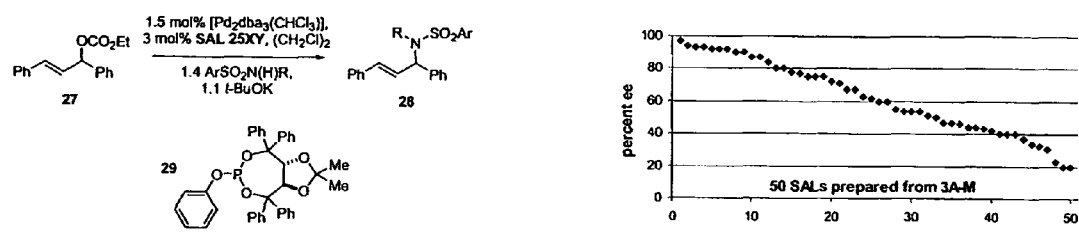

The selective formation of the heteroleptic (box)$_2$Zn complex is driven by the complementary chirality of the box subunits and is essentially independent of the nature of the remote substituents on each box ligand. A series of bifunctional ligands 24A-M were prepared (FIG. 11). For the purposes of this initial study the ligating group was kept constant, the choice of the TADDOL-derived monophosphite ligating group was more or less arbitrary. Treating complementary combinations of bifunctionalligands 24A-M with Zn(OAch is a simple way to prepare a library of SALs 25XY. We prepared 50 of the 169 possible combinations of subunits 24A-M. Each SAL 25XY bears two pendant TADDOL-derived monophosphites, thus the shape and electronic characteristics of the ligating groups are constant in this ligand library; only the ligand scaffold is varied. The idea was to determine whether the structure of the scaffold alone is sufficient to control the level of asymmetric induction exhibited by the derived catalyst systems. The SALs were screened in the palladium-catalyzed asymmetric allylic amination of racemic carbonate 27 by N-methyl-p-toluenesulfonamide. Chiral diphosphites have been employed in a wide range of asymmetric reactions, including palladium-catalyzed allylations; the latter are frequently used as a testing ground for new chiral ligand motifs. For reference, the corresponding allylic amination using two equivalents of ((R,R)-TADDOL)POPh (29, i.e., the same chiral ligating group without the SAL) gives (R)-28 (R=Me) in 48% ee.

The chiral diphosphites screened differ only in the structure of the self-assembled ligand scaffold, and while each gives predominantly (R)-28 (R=Me), the variation in enantioselectivity is striking. Plotting the results obtained for the 50 combinations of subunits A-M in descending order (FIG. 11), it can be seen that the enantiomeric excess varies almost linearly over a wide range (i.e., 20-97% ee). Two thirds of the SALs screened give a higher level of asymmetric induction than the monomer ((R,R)-TADDOL)POPh. While the goal, of course, is to obtain enantiomerically pure material directly from the reaction, products obtained at the level of 90% ee (95:5 er) are often practical; they can often be enriched to enantiomeric purity via one recrystallization with minimal losses. Nine combinations of SAL 25XY effect the asymmetric allylation in 90% ee or higher.

The variation in enantiomeric excess demonstrates the ability to use very subtle changes in the scaffold to manipulate the ligand topography around palladium. As tabulated in Table 1 each of the top catalysts contains one of two closely related subunits, F or H. These two tethers differ only in regard to the substitution pattern (1,3- vs. 1,4-) on the phenyl ring closest to the box subunit. The most successful ligand, 25FH, contains both subunits and affords 28 (R=Me) in 97% ee (entry 1). Surprisingly, the pseudo-C2-symmetric derivatives 25FF and 25HH are less effective, giving 84% and 87% ee respectively (entries 11 and 12). Compared to the latter two, the combinations 25FG and 25GH (entries 8 and 10; 90% and 87% ee) are similar to, perhaps slightly superior, and yet, 25GG is one of the worst combinations (entry 50,20% ee). The presence of F or H in and of itself does not guarantee success; 25AF is another of the worst combinations (entry 49, 20% ee). It is interesting to see that two poor subunits can form a favorable combination. Neither 25AA (60% ee) nor 25KK (31 % ee) are very good, but the combination 24AK at 75% ee is the best SAL lacking either an F or H subunit. When the substrate is changed, even modestly, SAL 25FH is no longer always the best choice. This highlights another feature of the self-assembly approach of the invention: easy ligand tunability. Chiral diphosphites 25FF, 25FH, and 25HH were screened with four other N-substituted sulfonamides giving the allylation product in high enantiomeric excess, for example (results for best SAL shown), N-(n-butyl) (25FF, 90% ee), -benzyl (25FH, 91 % ee), -isopropyl (25HH, 95% ee), and -phenyl (25FF, 88% ee).

TABLE 1

Data Summary Table 1. Screening SALs 25XY in the palladium-catalyzed allylic amination reaction with TsN(H)Me.

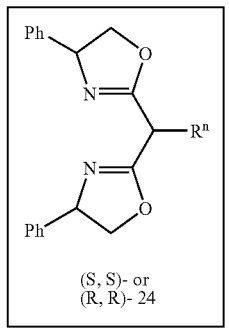

(S,S)- or (R,R)- 24

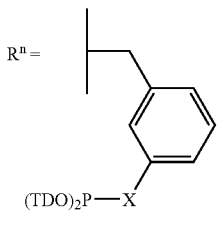

A (X = O)
B (X = OCH$_2$)

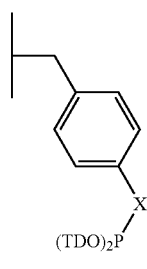

C (X = O)
D (X = OCH$_2$)

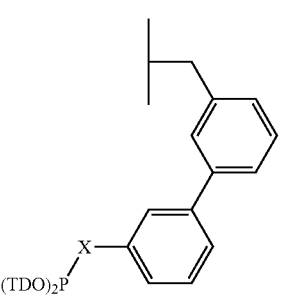

E (X = O)
F (X = OCH$_2$)

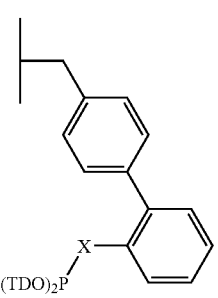

G (X = O)
H (X = OCH$_2$)

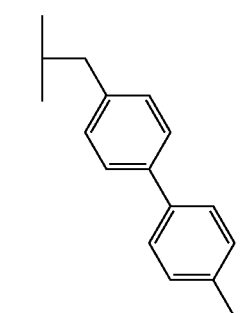

I (X = O)
J (X = OCH$_2$)

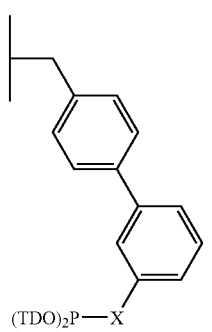

K (X = O)
L (X = OCH$_2$)

M

| | SAL | % ee |
|---|---|---|
| 1 | FH | 97 |
| 2 | FM | 94 |
| 3 | FJ | 93 |
| 4 | HJ | 93 |
| 5 | EH | 92 |
| 6 | FL | 92 |
| 7 | HL | 92 |
| 8 | GH | 90 |
| 9 | HM | 90 |
| 10 | FG | 87 |
| 11 | HH | 87 |
| 12 | FF | 84 |
| 13 | EF | 80 |
| 14 | FI | 80 |
| 15 | HK | 78 |
| 16 | FK | 77 |
| 17 | AK | 75 |
| 18 | AH | 75 |
| 19 | HI | 75 |
| 20 | IM | 72 |
| 21 | II | 71 |
| 22 | CF | 67 |
| 23 | IK | 67 |
| 24 | CH | 63 |
| 25 | EI | 62 |
| 26 | AA | 60 |
| 27 | CC | 60 |
| 28 | CK | 55 |
| 29 | GI | 54 |
| 30 | JM | 54 |
| 31 | MM | 54 |
| 32 | IJ | 51 |
| 33 | AC | 50 |
| 34 | CI | 47 |
| 35 | JK | 47 |
| 36 | JL | 46 |
| 37 | AI | 44 |
| 38 | GJ | 44 |
| 39 | CJ | 43 |
| 40 | EJ | 42 |
| 41 | BB | 40 |
| 42 | IL | 40 |
| 43 | JJ | 40 |
| 44 | EE | 37 |
| 45 | AJ | 34 |
| 46 | LL | 33 |
| 47 | KK | 31 |
| 48 | DD | 23 |
| 49 | AF | 20 |
| 50 | GG | 20 |

EXAMPLE 14

Figure 12:
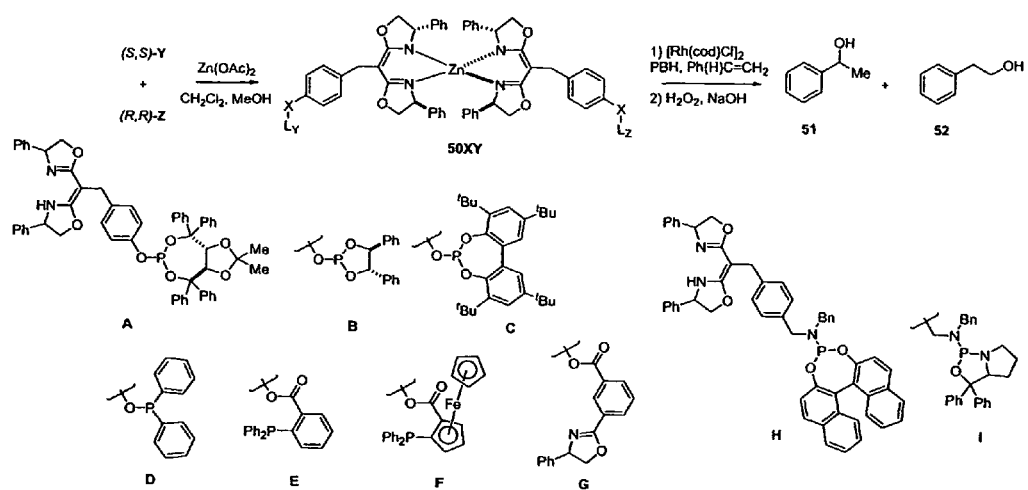
Figure 13:
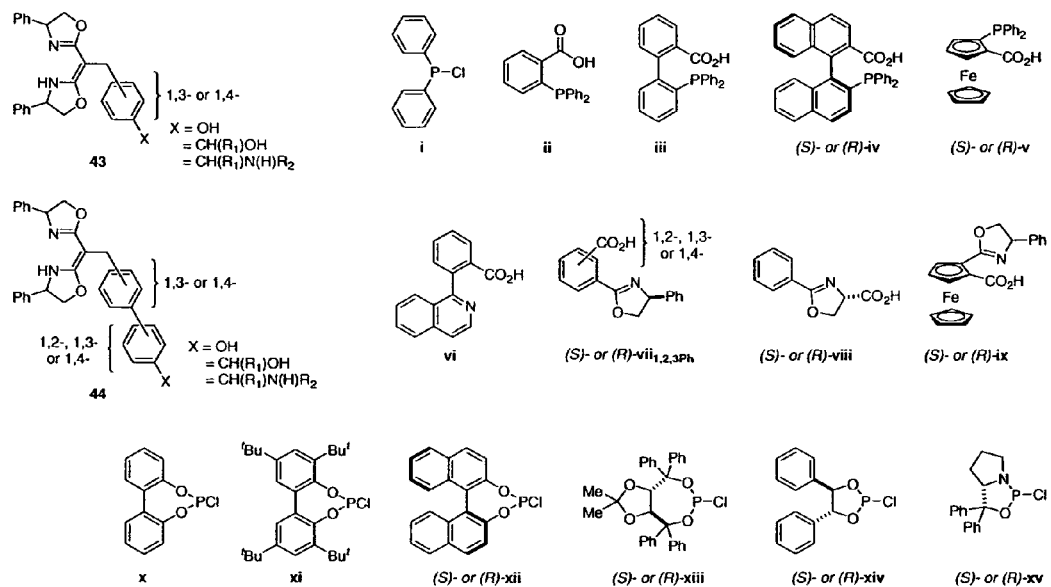
FIGS. 13-15 set forth structural formulae for various of the compounds described herein.

Studies on the hydroboration of styrene were carried out using a screening set of SALs. Two simple tethers were chosen, one phenol and one benzyl amine. Prepared derivatives A-H are illustrated in FIG. 12. Combinations of A-H using the Zn(Oac)$_2$ protocol afford a small screening set of SALs 50XY. Some preliminary data obtained with them are summarized in Table 2. Since the scaffold is not optimized at this stage, it was not expected to obtain the highest possible enantiomeric excess. However, useful information can be obtained from the relative activity of the catalysts from the various combinations, and in the case of styrene, the regioselectivity (i.e., branched versus linear alcohol). To get a rough measure catalyst activity, each reaction was run for the same standard time; consequently, the observed yield is a measure of catalyst turnover frequency and/or number.

TABLE 2

[(50XY)Rh(cod)Cl]-catalyzed hydroboration of styrene.
The product is predominantly R.

| Entry | 50XY | Yield (%) | 51:52 | ee (%) |
|-------|------|-----------|-------|--------|
| 1 | AA | 98 | 2.5:1 | 76 |
| 2 | AB | 88 | 1.5:1 | 2 |
| 3 | AC | 90 | 6.1:1 | 46 |
| 4 | AD | 90 | 4.3:1 | 60 |
| 5 | AE | 30 | 1:1.3 | 3 |
| 6 | AH | 95 | 6.6:1 | 78 |
| 7 | BB | 75 | 1:1 | 0 |
| 8 | BD | 85 | 2:1 | 17 |
| 9 | BF | 95 | 4:1 | 7 |
| 10 | BG | 99 | 2:1 | 14 |
| 11 | CF | 80 | 10:1 | 8 |
| 12 | CG | 90 | 15:1 | 7 |
| 13 | CH | 90 | 6.9:1 | 4 |
| 14 | DD | 26 | 1:1.1 | 3 |
| 15 | EI | 50 | 1:2.5 | 4 |
| 16 | FI | 35 | 1:1.2 | 30 |
| 17 | GG | 41 | 1:1.1 | 3 |
| 18 | GI | 90 | 1:3 | 10 |

The results in Table 2 are very encouraging. They demonstrate that one can successfully use SALs in this reaction, and as expected, the various combinations 50XY show a wide range of behavior: yields vary from no reaction (50H1, data not shown) to near quantitative (50BG, entry 10); regioselectivity varies from 15:1 favoring the branched alcohol (50CG, entry 12) to 1:3 favoring the achiral linear isomer (50GI, entry 18); and the enantioselectivity reaches as high as 78%. This means that the elements in the SAL which can be varied are very much involved in determining reaction selectivity. For example, it is particularly striking how strongly the presence of subunit C improves the regioselectivity toward the desired branched isomer.

EXAMPLE 15

Rhodium-Catalyzed Asymmetric Hydrogenation

The need to carry out enantioselective hydrogenation is frequently encountered in chemical discovery and process research. Such processes are relevant to the production of a wide range of synthetic intermediates andare of substantial industrial importance. There exist significant drawbacks to carrying out these types of reactions utilizing currently available catalyst systems. The reaction also constitutes a common testing ground for new ligand systems for asymmetric catalysis. Having used palladium-catalyzed allylic amination to demonstrate proof of principle for the method of the invention above, asymmetric hydrogenation offers the opportunity to evaluate the approach with a different metal and in very different reaction.

A new concept in asymmetric catalysis has previously been reported, i.e., the idea of screening combinatorial mixtures of simple monodentate ligands. In rhodium-catalyzed hydrogenation reactions, prior researchers found that the enantiomeric excess obtained from certain mixtures of ligands was higher than that obtained with either ligand alone.

Figure 14:
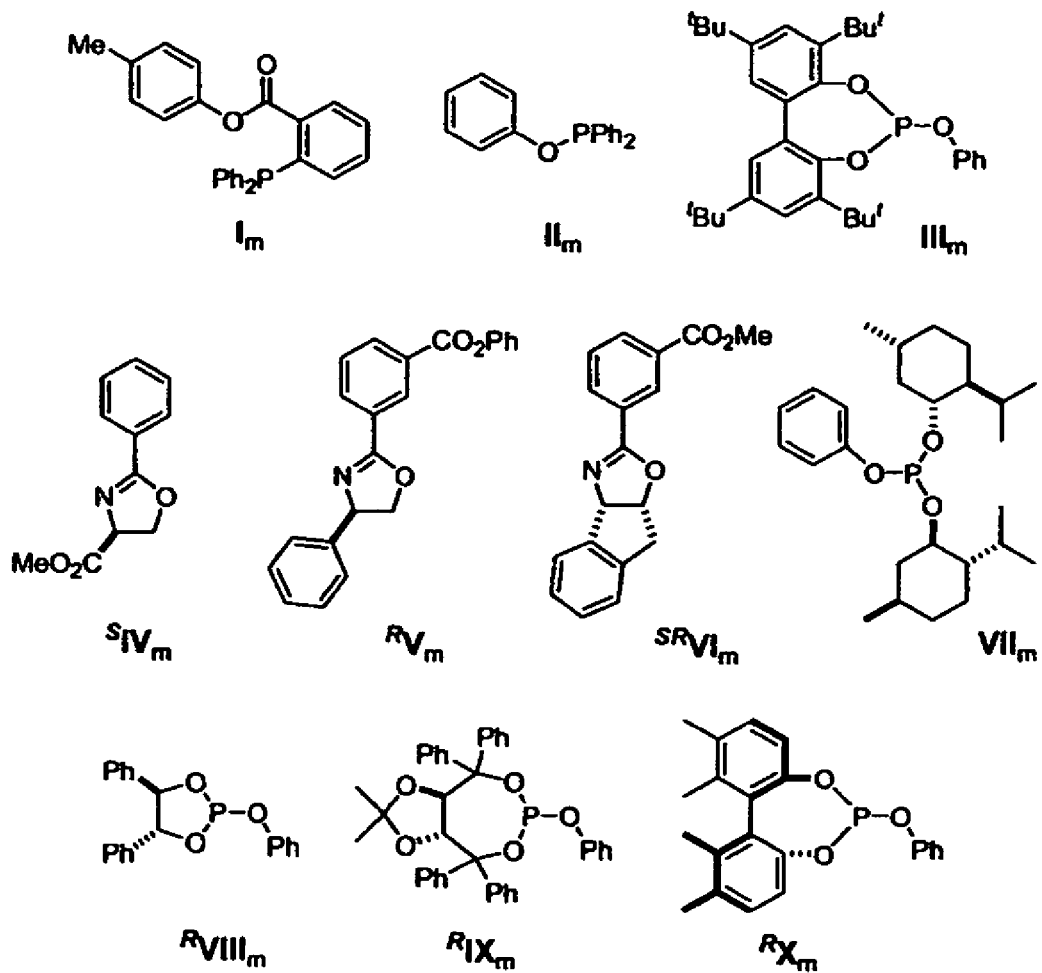

In the SAL approach of the present invention, there exists considerable flexibility as to the choice of ligating groups. Thus, it is desirable to select the combination(s) of ligating groups that will most likely afford efficient catalysts (efficiency as defined by yield and reaction rate as well as selectivity), and then rely on the ability to vary the SAL scaffold to optimize their orientation and hence the enantioselectivity. To aid in selecting the most promising ligating group(s) for preparing the SAL library, various combinations of the monomeric model ligands ($I_m$–$X_m$) shown in FIG. 14 were screened in the rhodium-catalyzed hydrogenation of the amino acid precursor, enamide 7. The monomeric ligands shown correspond to ligating groups that could readily be incorporated in the SAL precursors described above.

TABLE 3

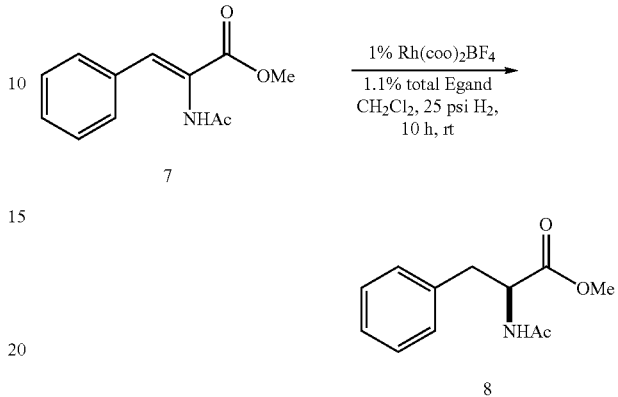

| | (S)-$IV_m$ | (R)-$V_m$ | $VI_m$ | $VII_m$ | $VIII_m$ | $IX_m$ | (R)-$X_m$ |
|---|---|---|---|---|---|---|---|
| $I_m$ | 5 (5 S) | 5 (1 S) | 13 (5 S) | 10 (7 R) | 100 (5 R) | 10 (2 S) | 1 (5 S) |
| $II_m$ | 93 (rac) | 99 (1 S) | 26 (3 S) | 100 (1 S) | 100 (5 S) | 90 (1 R) | 99 (7 S) |
| $III_m$ | 68 (rac) | 94 (rac) | 55 (8 R) | 100 (3 R) | 100 (12 S) | 100 (1 S) | 89 (13 S) |
| (S)-$IV_m$ | 17 (10 R) | 7 (1 S) | 3 (8 S) | 18 (33 R) | 98 (8 R) | 15 (3 S) | 42 (57 S) |
| (R)-$V_m$ | | 20 (26 R) | 42 (43 R) | 16 (29 R) | 97 (rac) | 14 (3 S) | 37 (61 S) |
| $VI_m$ | | | 5 (4 S) | 14 (6 S) | 24 (2 R) | 3 (10 R) | 19 (43 S) |
| $VII_m$ | | | | 24 (34 R) | 100 (4 R) | 19 (4 S) | 98 (57 S) |
| $VIII_m$ | | | | | 100 (11 R) | 100 (4 R) | 100 (rac) |
| $IX_m$ | | | | | | 100 (2 S) | 100 (76 S) |
| (R)-$X_m$ | | | | | | | 100 (65 S) |

$^m$The table entries refer the combination of ligands (0.55 mole percent of each) used for that reaction; the chemical yields are shown along with the % ee's obtained and the major enantiomer formed given in parentheses. For example, data in the first row show the results obtained using the combination of 0.55 mole percent of ligand $I_m$ with 0.55 mole percent of each of the chiral monomeric ligands $^S IV_m$ through $^R X_m$.

The tabulated screening data (Table 3) provide a great deal of information. The goal of the study is not to necessarily identify the optimal monodentate ligand for the reaction; others have successfully pursued that approach as described above. Rather, the purpose is to identify promising ligating groups that can readily be incorporated into SAL precursors to prepare SAL libraries with which the potential for ligand tuning via scaffold optimization can be evaluated. The various combinations of ligands $I_m$–$X_m$ give rise to wide variations in yield and enantioselectivity in the rhodium-catalyzed asymmetric hydrogenation of enamide 7. The axially chiral BIPHEP phosphite derivative $^S X_m$ stands out as the most interesting ligand screened. Almost every combination with it gives an appreciable level of enantioselectivity. Its heterocombination with the TADDOL derivative $^R IX_m$ is particularly intriguing. Considering the data in Table 1, the BIPHEP phosphite ligating group appears to be the obvious lead structure for an initial SAL library.

Figure 15:
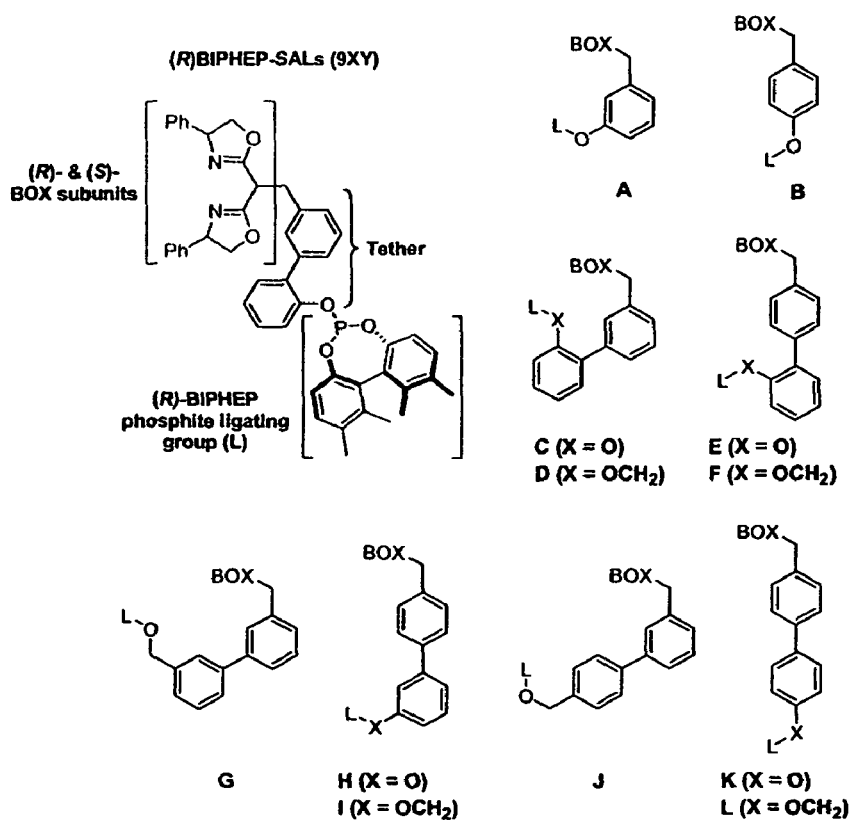

Investigating a combinatorial library of (R)BIPHEP-SALs involved the preparation and screening of a library of 110 SAL combinations (i.e., SAL-9XY) in the rhodium-catalyzed hydrogenation of the amino acid precursor, enamide 7. The SALs screened were drawn from the set of subunits illustrated in FIG. 15 (i.e., SAL subunits A-L). Each subunit contains the BIPHEP phosphite ligating group, and for the most part, the SALs used in the [(SAL9XY)Rh(BF$_4$)]-catalyzed asymmetric hydrogenations of enamide 7 were prepared in situ by combining the desired two SAL subunits with Et$_2$Zn.

Figure 16:
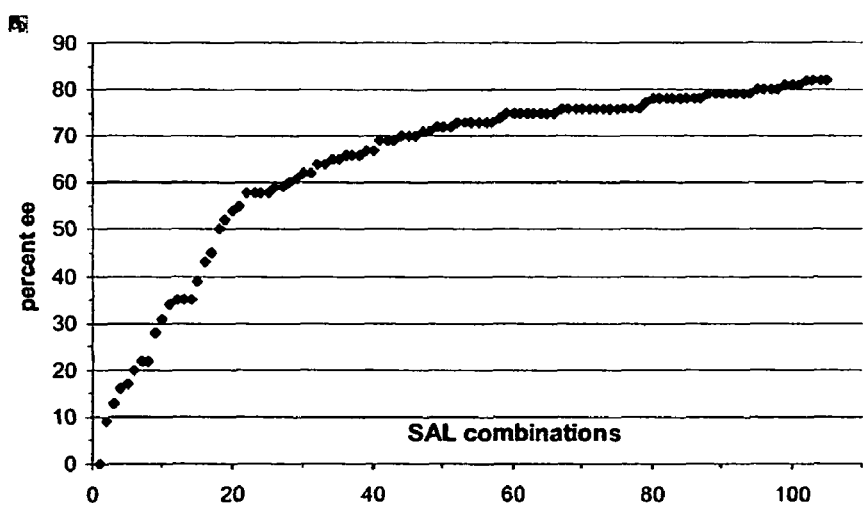

FIG. 16 shows the variation in enantioselectivity obtained as a function of the SAL scaffold for the 110 SAL-9XY (X and Y independently selected from among A through L) combinations screened in the present study; the percent ee obtained is plotted from low to high. For reference, using two equivalents of chiral monophosphite (BIPHEP)POPh ($X_m$) gives 65% ee in the reaction. Once again, wide variation exists in enantioselectivity, from racemic to above 80% ee, with roughly two thirds of the SAL-9XY combinations affording a higher level of asymmetric induction than the model monomer $X_m$. The results of the screening reactions reflect only the influence of varying the scaffold structure; every SAL in the screen has the same set of BIPHEP ligating groups. The graph is qualitatively similar to that seen for the palladium-catalyzed asymmetric allylic amination reported above; however, unlike that study, here, the plot levels off.

Apparently, many of the variations in scaffold are effectively redundant; that is, they do not significantly alter the topography defined by the BIPHEP phosphite moiety in the chiral rhodium catalyst. The results suggest that a more diverse set of SAL subunits is needed to further optimize the scaffold structure or that the limit of the capacity to productively orient the BIPHEP phosphite moiety has been reached. Nonetheless, the best SAL combinations identified thus far are already very close to giving useful levels of asymmetric induction.

TABLE 4

[(SAL-9XY)Rh(BF$_4$)]-Catalyzed asymmetric hydrogenation of dehydroaminoacid derivative 7 using various combinations of BIPHEP-SAL subunits A-L.$^a$

| SAL-9XY | R-A | R-B | R-C | R-D | R-E | R-F | R-H | R-I | R-J | R-L |
|---|---|---|---|---|---|---|---|---|---|---|
| S-A | 49 | 66 | 16 | 78 | 35 | 78 | 100 | 49 | 23 | 75 |
|  | (62) | (79) | (61) | (73) | (59) | (75) | (72) | (73) | (71) | (69) |
| S-B | 50 | 69 | 7 | 61 | 26 | 79 | 97 | 47 | 46 | 49 |
|  | (69) | (76) | (58) | (75) | (64) | (78) | (81) | (78) | (76) | (72) |
| S-C | 5 | 18 | 3 | 52 | 2 | 66 | 35 | 33 | 24 | 17 |
|  | (57) | (70) | (58) | (78) | (58) | (79) | (43) | (76) | (75) | (73) |
| S-D | 4 | 1 | 2 | 51 | 1 | 73 | 17 | 71 | 54 | 35 |
|  | (34) | (35) | (13) | (79) | (35) | (80) | (35) | (79) | (79) | (75) |
| S-E | 6 | 11 | 4 | 24 | 3 | 43 | 23 | 47 | 34 | 27 |
|  | (41) | (66) | (rac) | (70) | (9) | (75) | (22) | (73) | (69) | (65) |
| S-F | 13 | 55 | 7 | 81 | 9 | 87 | 42 | 92 | 90 | 70 |
|  | (64) | (72) | (59) | (82) | (67) | (81) | (45) | (82) | (82) | (80) |
| S-G | 10 | 54 | 10 | 60 | 11 | 35 | 61 | 31 | 25 | 45 |
|  | (62) | (73) | (58) | (80) | (69) | (78) | (50) | (76) | (76) | (78) |
| S-H | 13 | 46 | 14 | 59 | 6 | 28 | 18 | 100 | 44 | 66 |
|  | (31) | (60) | (17) | (74) | (28) | (71) | (16) | (76) | (55) | (66) |
| S-I | 21 | 96 | 38 | 96 | 58 | 97 | 94 | 97 | 82 | 96 |
|  | (53) | (76) | (76) | (77) | (73) | (81) | (54) | (79) | (76) | (76) |
| S-J | 28 | 95 | 44 | 92 | 30 | 93 | 98 | 67 | 57 | 37 |
|  | (65) | (75) | (66) | (78) | (67) | (80) | (52) | (76) | (78) | (76) |
| S-K | 10 | 28 | 1 | 38 | 1 | 89 | 10 | 68 | 13 | 26 |
|  | (52) | (70) | (22) | (78) | (39) | (82) | (20) | (79) | (75) | (75) |

The detailed results of the screening reactions are summarized in Table 4. Again, the data demonstrate wide variation in both yield and enantioselectivity for the [(SAL-9XY)Rh(BF$_4$)]catalyzed asymmetric hydrogenation. While the latter ranges from racemic to above 80% ee, the S-enantiomer predominates in all non-racemic products obtained. Eleven combinations (i.e., those highlighted in boldface in Table 4) give 80% ee or greater. An interesting trend emerges from the data obtained with this combinatorial library of 110 SALs. Nine of the eleven most successful combinations contain subunit F; for example, the combination using two F subunits, SAL-9FF, is among the best, affording 81% ee (87% yield).

However, small changes in the SAL scaffold can result in large differences in enantioselectivity and yield. For example, contrast the results obtained using SAL-9FF (81% ee, 87% yield) to those obtained using the closely related structure SAL-9EE (9% ee, 3% yield). While each of the SALs in Table 4 is structurally unique, some differ only very subtly in scaffold structure. For example, SAL-9FI can be prepared by combining (S)-F with (R)—I or by combining (R)- F with (S)-1. The resulting diastereomeric SALS generally behave similarly, 82% ee (92% yield) and 81% ee (97% yield), respectively, for the two combinations described.

The results obtained thus far make it clear that, while the shape of the BIPHEP-phosphite ligating group within the macro cyclic metal chelate is invariant, small changes in the ligand scaffold reposition or reorient that shape to a more, or less, effective position for asymmetric catalysis.

Suitable ligands and tethers are exemplified above; however, it will be apparent to those skilled in the art that many more such groups may be employed in the practice of the invention and that the identification thereof would not require the exercise of inventive faculties.

The invention claimed is:

1. A heteroleptic, multiple metal-containing metallocyclic catalyst having the formula:

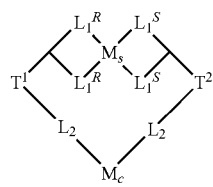

wherein: $L_1^S$ and $L_1^R$ are each ligating functional groups of complementary chirality, said $L_1^S$ having a counter-clockwise configuration and said $L_1^R$ having a clockwise configuration;

wherein said $M_s$ is a scaffold-structural metal and wherein the scaffold-structural metal is Zn(II) or Co(II);

wherein said $M_c$ is a catalytic metal and wherein the catalytic metal is Rh(I), Pd(II) or Ir(I);

wherein each of said $L_2$ is a ligating functional group;

wherein said $T_1$ and $T_2$ are each tethers;

wherein each of said $L_1^s$ and $_1^R$ is capable of ligating said $M_s$;

wherein each of said $L_2$ is capable of ligating said M;

wherein said $T_1$ links each of said $L_1^R$ and is connected to at least one of said $L_2$; and wherein said $T_2$ links each of said $L_1^s$ and is connected to at least one of said $L_2$.

2. The catalyst of claim 1, wherein the ligating functional groups are (TADDOL)P—, (BINOL)P—, or (BIPHEP)P— derivatives, said derivatives selected from the group of derivatives consisting of (TADDOL)P—, (BINOL)P— or (BIPHEP)P— phosphites; (TADDOL)P—, (BINOL)P— or (BIPHEP)P— phosphoramidites;

and (TADDOL)P—, (BINOL)P— or (BIPHEP)P— phosphinites.

3. The catalyst of claim 2, wherein the ligating functional groups are (TADDOL)P—, (BIINOL)P— or (BIPHEP)P— phosphites.

4. The catalyst of claim 2, wherein the ligating functional groups are (TADDOL)P—, (BINOL)P— or (BIPHEP)P— phosphoramidites.

5. The catalyst of claim 2, wherein the ligating functional groups are (TADDOL)P—, (BINOL)P— or (BIPHEP)P— phosphinites.

6. The catalyst of claim 1, wherein the ligating functional groups are at least one of

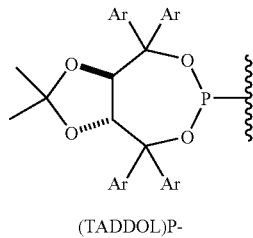

(TADDOL)P-

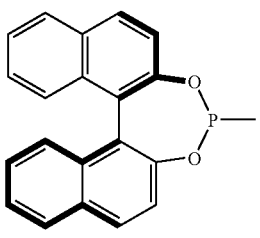

(BINOL)P-

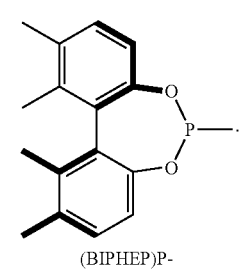

(BIPHEP)P- a: Ar = Ph
b: Ar = (3,5-Me)C$_6$H$_4$
c: Ar = (p-Me)C$_6$H$_4$
d: Ar = (p-tBu)C$_6$H$_4$

7. The catalyst of claim 1, wherein the ligating functional groups are selected from the group consisting of (TADDOL)P—, (BINOL)P—, and (BIPHEP)P— phosphites; and wherein the catalytic metal is selected from the group consisting of Rh(I), Pd(II) and Ir(I).

8. The catalyst of claim 1 having the formula:

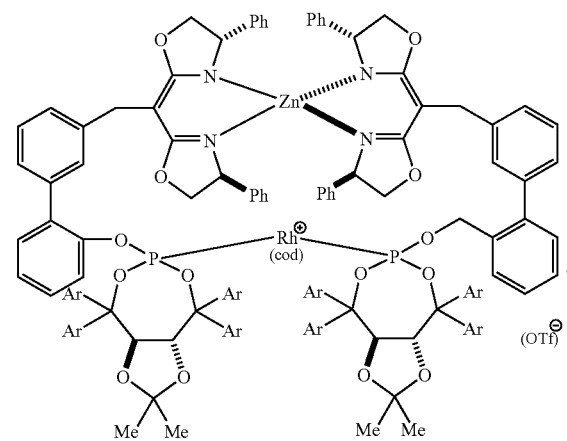

9. The catalyst of claim 1, having the formula:
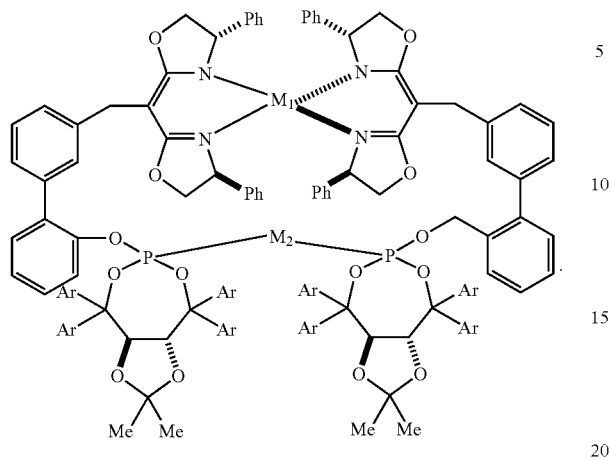
10. The catalyst of claim 1, wherein the tethers are at least one of:
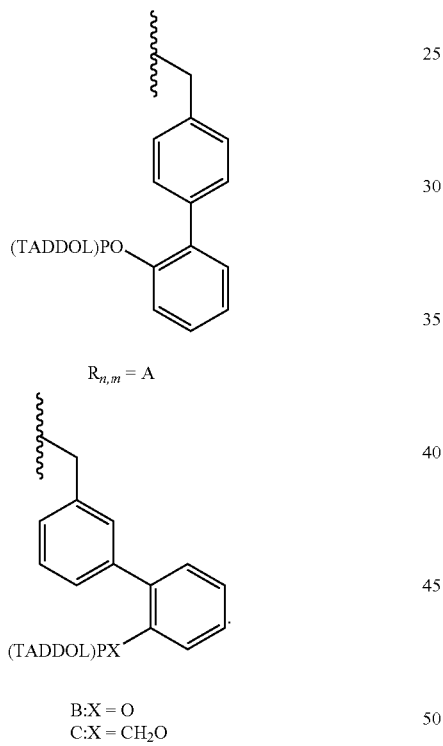
B: X = O
C: X = CH₂O
11. The catalyst of claim 1, wherein the tethers are at least one of
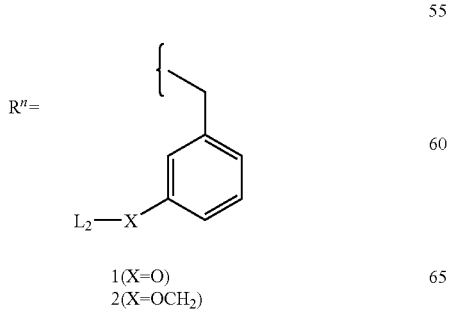
1 (X = O)
2 (X = OCH₂)
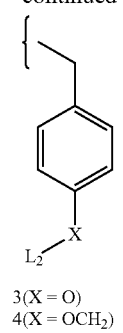
3 (X = O)
4 (X = OCH₂)
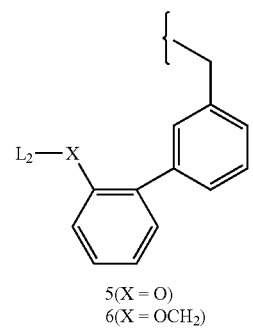
5 (X = O)
6 (X = OCH₂)
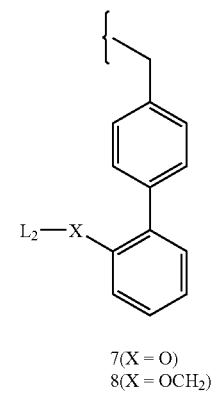
7 (X = O)
8 (X = OCH₂)
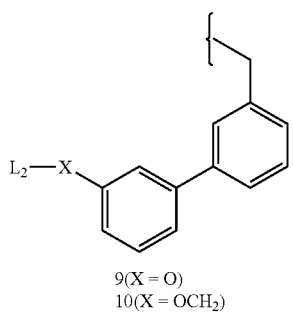
9 (X = O)
10 (X = OCH₂)

-continued

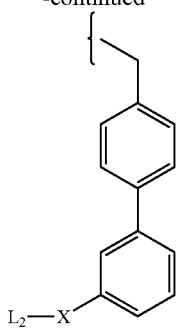

11(X = O)
12(X = OCH₂)

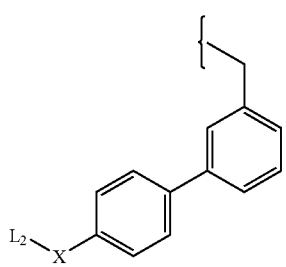

13(X = O)
14(X = OCH₂)

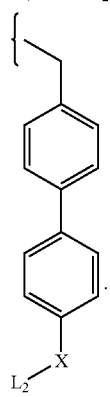

15(X = O)
16(X = OCH₂)

12. The catalyst of claim 1, wherein the tethers are:

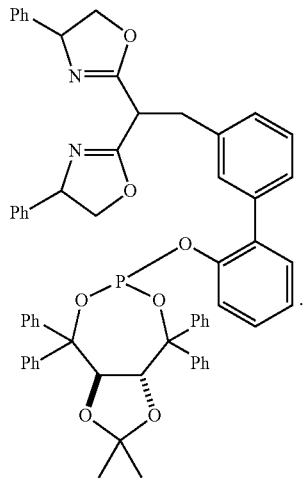

13. The catalyst of claim 7, wherein the scaffold-structural metal is Zn(II) or Co(II).

14. The catalyst of claim 1, wherein the catalytic metal is Rh(I).

15. The catalyst of claim 1, wherein the catalytic metal is Ir(I).

16. The catalyst of claim 1, wherein the catalytic metal is Pd(II).

17. The catalyst of claim 1, wherein the scaffold-structural metal is Zn(II).

18. The catalyst of claim 1, wherein the scaffold-structural metal is Co(Il).

\* \* \* \* \*